(12) United States Patent
Eaton-Evans et al.

(10) Patent No.: US 12,144,538 B2
(45) Date of Patent: Nov. 19, 2024

(54) ABLATION PROBE

(71) Applicant: National University of Ireland, Galway, Galway (IE)

(72) Inventors: Jimmy Eaton-Evans, Galway (IE); Giuseppe Ruvio, Galway (IE); Jonathan Bouchier-Hayes, Galway (IE); Martin O'Halloran, Galway (IE); Mark Bruzzi, Galway (IE)

(73) Assignee: NATIONAL UNIVERSITY OF IRELAND, GALWAY, Galway (IE)

( * ) Notice: Subject to any disclaimer, the term of this patent is extended or adjusted under 35 U.S.C. 154(b) by 1087 days.

(21) Appl. No.: 17/043,417

(22) PCT Filed: Mar. 29, 2019

(86) PCT No.: PCT/EP2019/058072
§ 371 (c)(1),
(2) Date: Sep. 29, 2020

(87) PCT Pub. No.: WO2019/185905
PCT Pub. Date: Oct. 3, 2019

(65) Prior Publication Data
US 2021/0113261 A1    Apr. 22, 2021

(30) Foreign Application Priority Data

Mar. 29, 2018 (WO) ............... PCT/EP2018/058252
Sep. 28, 2018 (EP) ................................. 18197568

(51) Int. Cl.
*A61B 18/18*    (2006.01)
*A61B 18/14*    (2006.01)
*A61B 18/00*    (2006.01)

(52) U.S. Cl.
CPC .............. *A61B 18/1477* (2013.01); *A61B 2018/00023* (2013.01); *A61B 2018/00077* (2013.01);
(Continued)

(58) Field of Classification Search
CPC ...... A61B 2018/00178; A61B 18/1477; A61B 2018/00023; A61B 2018/00077;
(Continued)

(56) References Cited

U.S. PATENT DOCUMENTS 3,668,573 A * 6/1972 Martin .................. H01P 3/00
333/237
4,366,457 A * 12/1982 Bode .................. H01Q 13/203
333/237
(Continued)

FOREIGN PATENT DOCUMENTS

CN    102014779 A    4/2011
CN    102727306 A    10/2012
(Continued)

OTHER PUBLICATIONS

International Search Report and Written Opinion issued in PCT Application Serial No. PCT/EP2019/058072 on Jul. 8, 2019; 12 pages.
(Continued)

*Primary Examiner* — Michael F Peffley
*Assistant Examiner* — Amanda L Zink
(74) *Attorney, Agent, or Firm* — Brian J. Colandreo; Jeffrey T. Placker; Holland & Knight LLP

(57) ABSTRACT

An ablation probe (1; 100; 200), comprising: an applicator (2; 102; 202) arranged to apply radiation to heat surrounding tissue; a feeding cable (4; 104; 204) arranged to supply electromagnetic energy to the applicator. The feeding cable comprises a distal portion (2a, 202a) and a proximal portion (2b; 202b). The distal portion of the feeding cable has a distal cross sectional size and the proximal portion of the feeding cable has a proximal cross sectional size, wherein the distal cross sectional size is less that the proximal cross sectional size. The ablation probe further comprises a con-
(Continued)

nector (24; 224) arranged to mechanically and electrically couple the distal portion (2a, 202a) of the feeding cable (2; 202) to the proximal portion (2b; 202b) of the feeding cable (2; 202). The connector comprises a joining member (12) comprising a proximal end (12b) shaped to receive an end of the proximal portion (2b; 2b) of the feeding cable and a distal end (12a) shaped to receive an end of the distal portion (2a; 202a) of the feeding cable.

18 Claims, 8 Drawing Sheets

(52) U.S. Cl.
CPC ............... *A61B 2018/00178* (2013.01); *A61B 2018/00577* (2013.01); *A61B 2018/1435* (2013.01)

(58) Field of Classification Search
CPC ........... A61B 2018/00285; A61B 2018/00577; A61B 2018/1435; A61B 2018/1869
See application file for complete search history.

(56) References Cited

U.S. PATENT DOCUMENTS

| | | | | |
|---|---|---|---|---|
| 4,967,765 | A | * | 11/1990 | Turner ............... A61B 18/1815 600/549 |
| 5,275,597 | A | * | 1/1994 | Higgins ................. A61B 17/22 607/116 |
| 5,755,465 | A | * | 5/1998 | Stewart, Jr. ........ H02G 15/1806 174/DIG. 8 |
| 2005/0015081 | A1 | | 1/2005 | Turovskiy et al. |
| 2005/0165389 | A1 | | 7/2005 | Swain et al. |
| 2005/0245920 | A1 | * | 11/2005 | Vitullo .................. A61B 18/18 607/156 |
| 2008/0051776 | A1 | | 2/2008 | Bliweis et al. |
| 2008/0135288 | A1 | | 6/2008 | Taylor et al. |
| 2010/0045558 | A1 | | 2/2010 | Rossetto |
| 2011/0180323 | A1 | | 7/2011 | Luzzi |
| 2012/0143180 | A1 | | 6/2012 | Lee, Jr. et al. |
| 2012/0259326 | A1 | | 10/2012 | Brannan et al. |
| 2013/0178841 | A1 | | 7/2013 | Reid, Jr. |
| 2013/0345699 | A1 | | 12/2013 | Brannan et al. |
| 2014/0128862 | A1 | * | 5/2014 | Rossetto ............... A61B 18/14 606/33 |
| 2014/0276739 | A1 | | 9/2014 | Brannan et al. |
| 2017/0273737 | A1 | | 9/2017 | Iwanami et al. |
| 2018/0036081 | A1 | | 2/2018 | Dickhans et al. |
| 2021/0161586 | A1 | | 6/2021 | Eaton-Evans et al. |

FOREIGN PATENT DOCUMENTS

| | | |
|---|---|---|
| EP | 2508145 A1 | 10/2012 |
| EP | 3381393 A1 | 10/2018 |
| EP | 3278755 B1 | 5/2021 |
| JP | 357174 A | 3/1991 |
| JP | 2004187703 A | 7/2004 |
| JP | 2012187405 A | 10/2012 |
| JP | 2014-516616 A | 7/2014 |
| JP | 2015509390 A | 3/2015 |
| WO | 2009098513 A1 | 8/2009 |
| WO | 2009137819 A1 | 11/2009 |
| WO | 2011140087 A2 | 11/2011 |
| WO | 2017067910 A2 | 4/2017 |
| WO | 2018178317 A1 | 10/2018 |
| WO | 2019185905 A1 | 10/2019 |

OTHER PUBLICATIONS

Japanese Office Action issued in counterpart application Serial No. JP2019-554411 on Feb. 22, 2022.
First Office Action issued in Japanese Patent Application No. JP2020-552853 dated Jan. 10, 2023.
First Examination Report issued in Australian Application No. 2018242139 on Feb. 15, 2023.
First Office Action issued in Chinese Application No. 201880035175.2 on Nov. 3, 2022.

* cited by examiner

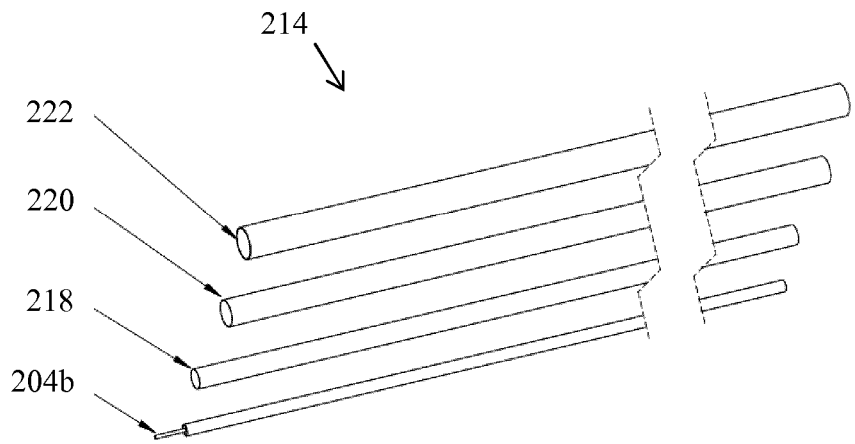
Figure 13
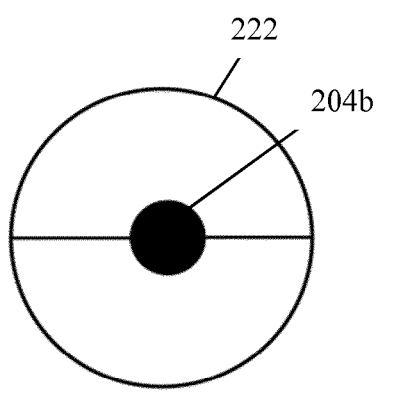 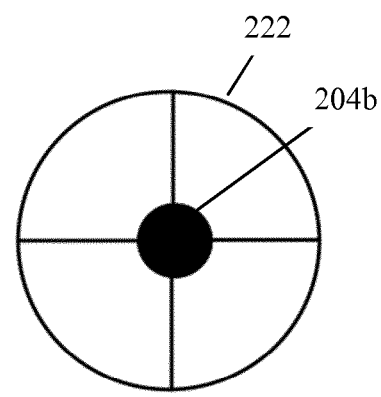 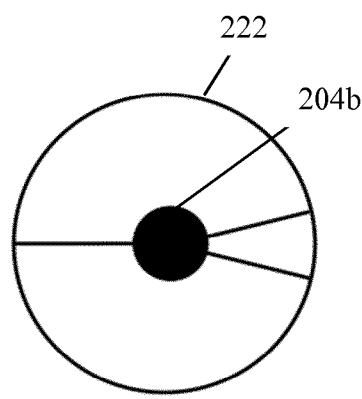
Figure 14a  Figure 14b  Figure 14c
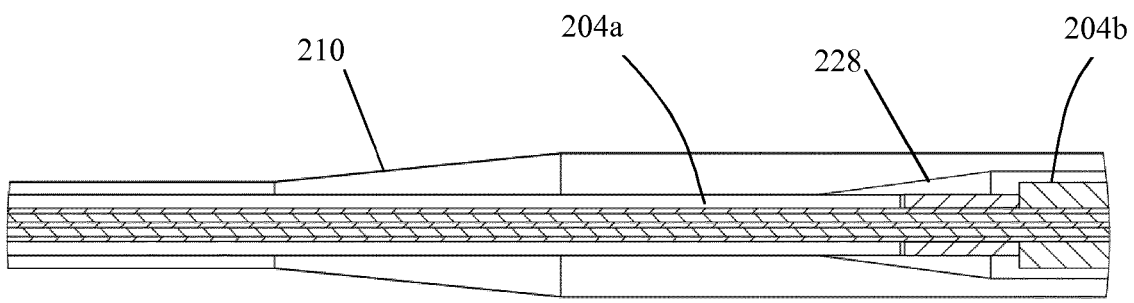
Figure 15a

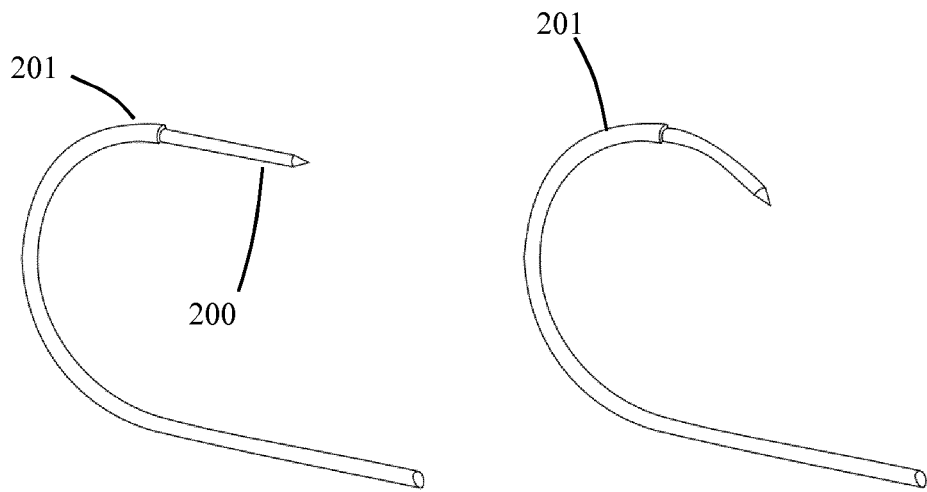
Figure 15b
Figure 15c
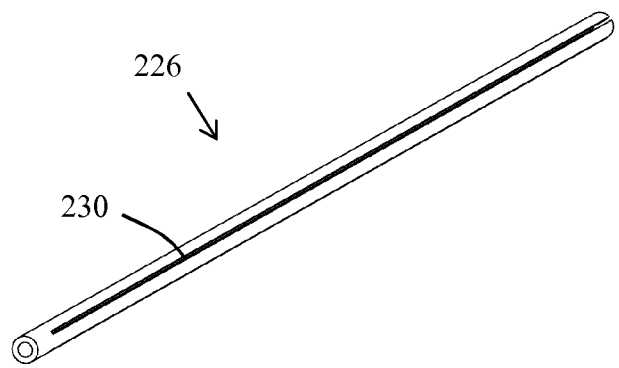
Figure 16
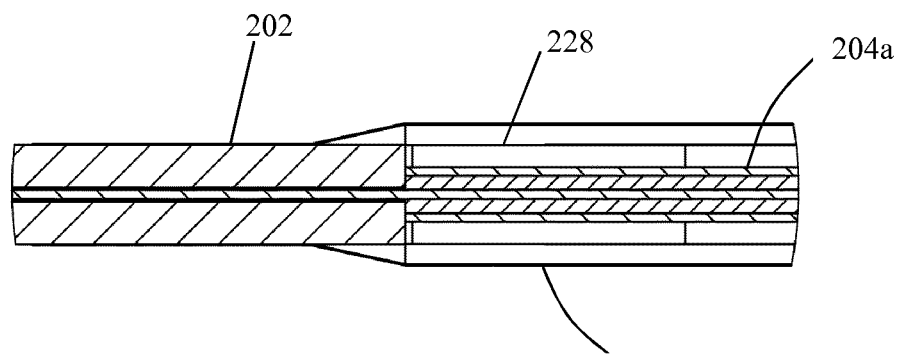
Figure 17

ABLATION PROBE

CROSS-REFERENCE TO RELATED APPLICATIONS

The subject application is a U.S. National Stage application of International Application No. PCT/EP2019/058072, filed on 29 Mar. 2019, which claims the priority of International Application Serial No. PCT/EP2018/058252, filed on 29 Mar. 2018 and European Patent Application Serial No. 18197568.1, filed on 28 Sep. 2018. The contents of all applications are herein incorporated by reference in their entirety.

This application relates to an ablation probe. In particular, this application relates to an ablation probe that may be used to generate heat within tissue to destroy tissue growths.

Thermal ablation can be used to destroy tissue growths within the body which can be malignant. Current ablation systems use applicators that deliver Radio Frequency (RF) energy (or microwave energy) to the tissue surrounding the applicator tip. This causes localised heating and destruction of the malignant cells. These applicators may be designed for percutaneous delivery and are therefore relatively short in length and large in diameter. However, many disease locations cannot be safely or easily accessed percutaneously. For example, the location of the pancreas behind the liver makes it difficult to access percutaneously. Similarly, access to the lung through the chest wall can cause a pneumothorax. Large diameter applicators may also cause undesired tissue damage during insertion. This limits the range of indications where thermal ablation therapy can be successfully delivered using existing percutaneous applicators.

Various sites within the human body can be accessed by navigating through a natural orifice. For example the periphery of the lung can be accessed using lung navigation systems, or similar devices such as an endoscope, that guide a working channel through the airway network to a target. This enables therapies to be delivered through the device working channel to diagnose and treat disease. Microwave ablation can be delivered via these systems. However, a long and flexible ablation catheter is required that is capable of delivering sufficient power to its radiating tip. Known microwave systems use coaxial cable to deliver power, with larger diameter cables used to generate fewer electrical losses than smaller gauge cables. However, small diameter cables improve flexibility, reduce insertion profile and require less force to straighten if plastically deformed during delivery. It is not practical to run a small cable (e.g. diameter <0.7 mm) over the length necessary to reach many target sites (e.g. >1 m for lung) because the electrical losses would be too great, and may result in excessive heating effects and insufficient power delivery (resulting in excessively long treatment times).

In the applicant's previous European application No. EP17164403.2 filed on 31 Mar. 2017, a microwave ablation probe having a feeding cable arranged to supply electromagnetic energy to an applicator was disclosed. The feeding cable comprises a proximal portion and a distal portion having different cross section sizes to each other. A connector is also provided to mechanically and electrically splice the distal portion of the feeding cable to the proximal portion. EP17164403.2 also disclosed the use of a deformable member which provides a coolant path through which coolant is able to flow.

The present application relates to improvements to the connector disclosed in EP17164403.2, and is applicable to ablation provides with and without coolant flow paths, and with or without a deformable member forming one of those coolant flow paths.

In one aspect, the present application provides an ablation probe, comprising:
  an applicator arranged to apply radiation to heat surrounding tissue;
  a feeding cable arranged to supply electromagnetic energy to the applicator,
  wherein the feeding cable comprises a distal portion and a proximal portion, wherein the distal portion of the feeding cable has a distal cross sectional size and the proximal portion of the feeding cable has a proximal cross sectional size, wherein the distal cross sectional size is less that the proximal cross sectional size; and
  a connector arranged to mechanically and electrically couple the distal portion of the feeding cable to the proximal portion of the feeding cable,
  wherein the connector comprises a joining member comprising a proximal end shaped to receive an end of the proximal portion of the feeding cable and a distal end shaped to receive an end of the distal portion of the feeding cable.

The ablation probe of the present application uses two sections of feeding cable, with one section being larger in cross sectional size than the other. The larger proximal portion of the feeding cable may enable efficient power delivery, while the smaller distal portion of the feeding cable may facilitate a smaller tissue insertion profile, greater catheter flexibility and allow improved resistance to permanent deformation of the cable. The ablation probe advantageously comprises a joining member formed from a separate component that may provide a short, mechanically strong, electrical coupling between the portions of the feeding cable. This may help to maintain overall flexibility, provide a small cross sectional profile and short length. As shown in the test results section provided later, the connector of the present application may help to provide low levels of electrical loss in the signal being transmitted to the applicator. These electrical losses would otherwise be manifest as heat, and may cause undesired heating of surrounding tissue at the position of the connector. Furthermore, any loss at the connector will reduce the level of electrical power transmitted to the applicator for use in ablation.

Optionally, the distal portion of the feeding cable may comprise: an inner conductor, an outer conductor, and a dielectric between them; and the proximal portion of the feeding cable may comprise an inner conductor, an outer conductor and a dielectric between them.

Optionally, the proximal end of the joining member may be arranged to fit around the outer conductor of the proximal portion of the feeding cable. This may provide a secure mechanical and electrical coupling between them.

Optionally, the proximal end of the joining member may be arranged to fit around an exposed portion of the dielectric of the proximal portion of the feeding cable, the exposed portion of the dielectric extending distally from a distal end of the outer conductor. This may help to provide a small overall cross sectional profile of the ablation probe.

Optionally, an outer surface of the joining member may be flush with outer surface of the outer conductor of the proximal portion of the feeding cable. This may provide a smooth outer surface of the ablation probe to aid insertion through the working channel of a delivery device.

Optionally, the inner conductors of each portion of the feeding cable may be electrically coupled within the body of the connector, and preferably the inner conductors may be coupled by a welded joint.

Optionally, the ablation probe may further comprise a tube arranged to house at least part of the distal portion of the feeding cable, and wherein a portion of the joining member is arranged to extend within the tube to form a mechanical coupling between them. This may help to provide a secure coupling to the distal portion of the feeding cable.

Optionally, at least part of the joining member may be air filled. This may help to provide impedance matching between the distal and proximal portions of the feeding cable. The low dielectric constant of the air may allow the overall size of the connector to be reduced.

Optionally, the joining member may comprise a dielectric member surrounding at least part of the length of the inner conductor of the proximal and/or distal portions of the feeding cable that extend within the joining member.

The dielectric member may extend (e.g. radially) between the inner conductor of the proximal or distal portion of the feeding cable and an inner surface of the joining member. Optionally, the dielectric member may be arranged to space apart (i.e. at a constant radial separation): the inner conductor of the proximal and/or distal portions of the feeding cable; and an inner surface of the joining member, so as to maintain constant separation between them (e.g. to prevent relative movement when the connector is bent during use). This may help provide constant impedance (which is proportional to the ratio between the diameter of the inner conductor, the inner diameter of the joining member and the dielectric properties of the dielectric between them).

Optionally, the dielectric member may comprise a spiral element. The spiral element may form a helix around a longitudinal axis of the inner conductor of the proximal and/or distal portion of the feeding cable. The use of the spiral (or helical) shape may provide flexibility, whilst also allowing reduced electrical losses and maintain constant separation between the inner conductors and the joining member inner wall.

Optionally, at least part of the joining member may be filled with a potting agent (for example a low-permittivity and/or heat resistant material that may be an epoxy). This may help improve the mechanical strength of the connector, and may mitigate the risk of coolant ingress.

Optionally, the joining member may further comprise a bleed hole, the bleed hole being configured to allow the flow of potting agent into or out of a cavity within the joining member. This may allow bleeding of the potting agent during assembly, and may avoid any undesired air pockets forming in the potting agent.

Optionally, an outer surface of the proximal end of the joining member may have a greater cross sectional size compared to an outer surface of the distal end of the joining member. The outer surface of the joining member may comprise a tapered portion extending at least partly between its proximal and distal ends. This may provide a smooth transition between the different sized parts of the joining member. Additionally or alternatively, the outer surface of the joining member may comprise a stepped portion disposed between its proximal and distal ends.

Optionally, an inner surface of the proximal end of the joining member may have a greater cross sectional size compared to an inner surface of the distal end of the joining member. The inner surface of the joining member may comprise a tapered portion extending at least partly between its proximal and distal ends. Additionally, or alternatively, the inner surface of the joining member may comprise a stepped portion disposed between its proximal and distal ends.

The tapered or stepped inner surface may aid impedance matching between the proximal and distal portions of the feeding cable.

Optionally, the joining member may be formed from a tubular member. The joining member may comprise a hypotube.

Optionally, the joining member may be formed from a flexible metal alloy, preferably Nitinol.

Optionally, the length of the joining member between its proximal and distal ends may be in the range between 5 and 15 mm.

Optionally, the diameter of the proximal portion of the feeding cable may be 0.031 inches (0.787 mm) and the diameter of the distal portion of the feeding cable may be 0.020 inches (0.508 mm).

In other embodiments: the diameter of the proximal portion may be 0.031 inches (0.787 mm) and the diameter of the distal portion may be 0.015 inches (0.381 mm); the diameter of the proximal portion may be 0.047 inches (1.194 mm) and the diameter of the distal portion may be 0.020 inches (0.508 mm); or the diameter of the proximal portion may be 0.034 inches (0.864 mm) and the diameter of the distal portion may be 0.043 inches (1.092 mm).

Optionally, the body of the joining member may comprise one or more weakened portions arranged to increase the flexibility of the joining member. The weakened portions may comprise one or more slots or cuts in the body of the joining member to increase its flexibility. The slots or cuts may be formed by laser cutting.

Optionally, the joining member may further comprise a heat transfer structure. The heat transfer structure may aid heat transfer from the joining member to the surroundings. The heat transfer structure may comprise one or more protrusions extending from the outer surface of the joining member.

Optionally, the connector may comprise a sealing member. The sealing member may be arranged to at least partially surround a connection region between the connector and either of the distal portion and proximal portions of the feeding cable. The sealing member may reduce or prevent water ingress into the connector. Optionally, the sealing member may comprise a polymer layer. The polymer layer may be formed by dipping the connector and feeding cable assembly into a polymer dip.

Optionally, the ablation probe may comprise a first coolant path and a second coolant path which form a coolant circuit arranged to deliver a flow of coolant to and away from the applicator. The reduced profile of the connector may allow the complete device assembly including the coolant circuit to fit within the working channel of a delivery device and function efficiently. The small profile of the connector may reduce the risk of occluding the coolant flow path resulting in impractical pumping pressures.

Optionally the ablation probe may further comprise: a first coolant flow path via which coolant is able to flow; and a deformable member arranged to move between an insertion configuration in which insertion of the probe is facilitated and a deployed configuration, wherein a second coolant path, via which coolant is able to flow, is provided by the deformable member when in the deployed configuration.

Optionally, the ablation probe may further comprise:
a. a needle portion comprising the deformable member, the applicator, the distal portion of the feeding cable, at least part of a tube housing at least part of the distal portion of the feeding cable and a distal portion of the first coolant path, and:

b. a catheter portion comprising the proximal portion of the feeding cable, the proximal portion of the first coolant path, and a coolant conduit, wherein the deformable member is fluidly connected to the coolant conduit at a boundary between the needle portion and the catheter portion and the coolant conduit is preferably a non-deformable coolant conduit.

Embodiments of the invention will now be described, by way of example only, with reference to the accompanying drawings, in which:

FIG. 13 shows an exploded view of a catheter portion of the ablation probe shown in FIG. 11;

Figure 11:
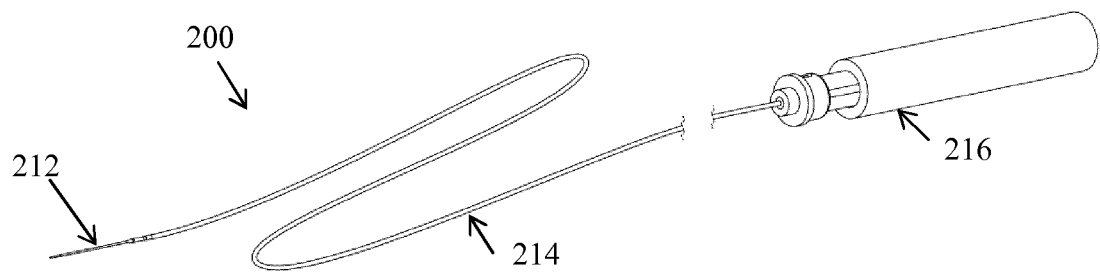
FIG. 11 shows a perspective view of an ablation probe according to an embodiment.
Figure 18:
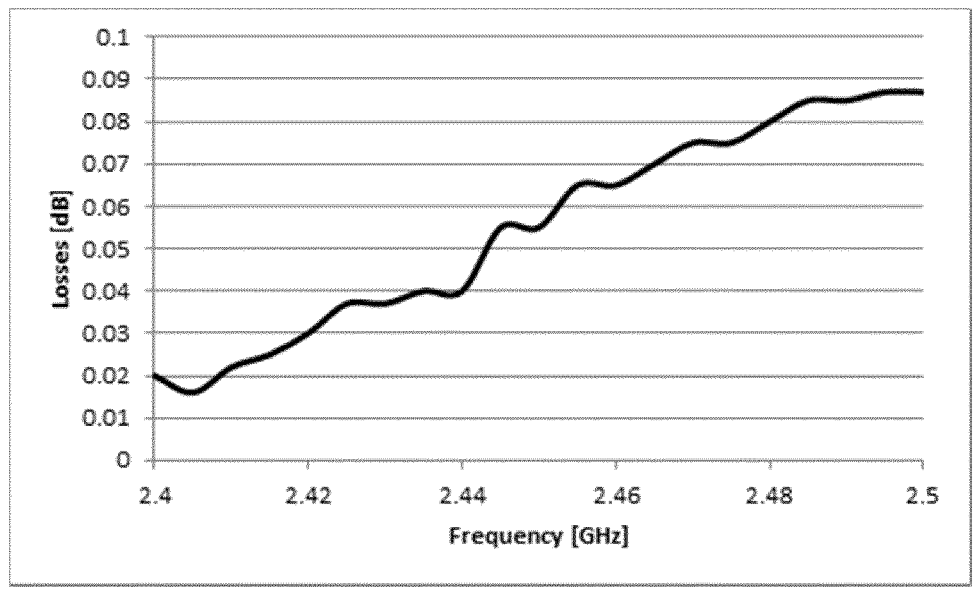

FIGS. 14a, 14b, and 14c show cross section views through a catheter portion of an ablation probe according to different embodiments;

FIG. 15a shows a close up view of the boundary between the needle portion and the catheter portion of the ablation probe shown in FIG. 11;

FIG. 15b shows a perspective view of an ablation probe having an tube formed from an elastic material extending from the distal end of a working channel along which it is inserted;

FIG. 15c shows a perspective view of an ablation probe without a tube formed from an elastic material extending from the distal end of a working channel along which it is inserted;

FIG. 16 shows a close up view of a tube forming part of the ablation probe shown in FIG. 11;

FIG. 17 shows another close up view of an embodiment of an applicator which may form part of the ablation probe shown in FIG. 11; and FIG. 18 shows a plot of electrical losses against frequency of the connector of an ablation probe according to an embodiment.

Figure 1:
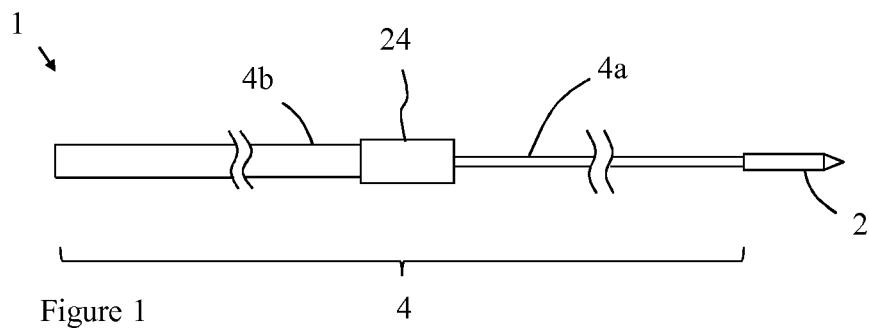
FIG. 1 shows a schematic view of an ablation probe according to an embodiment.

An ablation probe 1 according to one embodiment is shown schematically in FIG. 1. The ablation probe 1 of the present disclosure may be suitable for insertion into the body to reach a desired treatment site, such as a malignant tissue growth. In order to reach a desired treatment site, the ablation probe may be suitable for insertion through the working channel of an internal anatomy access device. By internal anatomy access device we mean any device which may be placed within the anatomy of a patient, the device having a working channel for insertion of instruments to a desired location within the body. The internal anatomy device may be an intraluminal delivery device arranged to be delivered along an anatomical lumen of the patient (e.g. the trachea and the pathways of the bronchi in the lungs or the oesophagus). The ablation probe 1 may, for example, be used endoscopically in order to reach a variety of disease locations within the body. The ablation probe may therefore have an overall flexibility such that it can be inserted through the working channel of the endoscope. In other embodiments, the ablation probe may be used with other types of intraluminal delivery device such as specific types of endoscope (e.g. a bronchoscope) or a navigation system such as a lung navigation system. In other examples, the ablation probe 1 may also be used percutaneously, or using any other suitable technique, e.g. inserted through an existing aperture of the body. For percutaneous use, the ablation probe may be generally rigid so that it can be inserted.

The ablation probe 1 comprises an applicator 2 arranged to apply radiation to heat surrounding tissue. The applied radiation may be adapted to cause localised heating and destruction of malignant cells around or near to the applicator 2. The applicator 2 may be arranged to apply any suitable form of radiation to surrounding tissue such that the desired heating is caused. The applicator 2 may, for example, be arranged to emit microwave or RF radiation, or may emit any other suitable radiation to cause heating. The applicator 2 may be arranged at or near a distal end of the ablation probe 1 so that it can be positioned in a desired position relative to the tissue to be treated. In the following, the terms "distal" and "proximal" are taken relative to the user operating the ablation probe and the treatment site when the ablation probe is positioned for use—the distal end of the ablation probe 1 is that closest to the treatment site and the proximal end is that closest to the user. A control means (not shown in the Figures) such as a handle may be provided at the proximal end of the ablation probe 1 so that it can be manipulated and positioned by the user. The ablation probe 1 may comprise a pointed distal tip adapted to piece tissue during use. In other embodiments, the ablation probe may comprise a blunt tip adapted to prevent or reduce the piercing of tissue during use. In such an embodiment, the applicator 2 may have a blunt distal end which is less likely to pierce tissue during use. This may be advantageous for some treatment sites such as in the lungs.

The ablation probe 1 further comprises a feeding cable 4 which is arranged to supply electromagnetic energy to the applicator 2. The feeding cable may be any elongate member suitable for supplying electromagnetic energy to the applicator (e.g. a conductor). The feeding cable 4 may run along at least part of the length of the ablation probe 1 to deliver a supply of energy to the applicator 2. In the described embodiment, a distal end of the feeding cable 4 is coupled to a proximal end of the applicator 2 and a proximal end of the feeding cable 4 is coupled to a generation means (not shown in the Figures) suitable for generating the desired signal to supply energy to the applicator 2.

The feeding cable 4 comprises a distal portion 4a and a proximal portion 4b. The distal portion 4a of the feeding cable has a distal cross sectional size and the proximal portion of the feeding cable has a proximal cross sectional size, wherein the distal cross sectional size is less that the proximal cross sectional size. In one embodiment, the diameter of the proximal portion 4b may be about 0.02 to 0.05 inches (about 0.508 to 1.27 mm) or about 0.02 inches or more (0.508 mm or more), and the diameter of the distal portion 4b may be about 0.01 to 0.04 inches (about 0.254 to 1.016 mm). In a preferred embodiment, the diameter of the proximal portion 4b is 0.031 inches (0.787 mm) and the diameter of the distal portion 4a is 0.020 inches (0.508 mm). In other embodiments: the diameter of the proximal portion 4b is 0.031 inches (0.787 mm) and the diameter of the distal portion 4a is 0.015 inches (0.381 mm); the diameter of the proximal portion 4b is 0.047 inches (1.194 mm) and the diameter of the distal portion 4a is 0.020 inches (0.508 mm); or the diameter of the proximal portion 4b is 0.034 inches (0.864 mm) and the diameter of the distal portion 4a is 0.043 inches (1.092 mm).

The sizes in the previous paragraph are the total overall cross section or diameter of the feeding cable. In other words, the part of the ablation probe formed by the distal portion of the feeding cable has a smaller overall cross section compared to the part formed by the proximal portion of the feeding cable. This means that the distal portion has a compact cross section more suited to extending from the end of the working channel of a delivery device, and being inserted into tissue to perform ablation.

The proximal portion of the feeding cable may be longer than the distal portion so as to provide power delivery along the length of the ablation probe used to reach a target ablation site within the body (e.g. when used with a delivery device such as an endoscope). The inner conductor 6b of the proximal portion 4b of the feeding cable may be greater in cross section compared to the inner conductor 6a of the distal portion 4a of the feeding cable 4 to allow efficient power delivery over its greater length. The inner conductor 6a of the distal portion 4a may have a diameter of about 0.002 to 0.008 inches (0.0508 to 0.2032 mm), and the inner conductor 6b of the proximal portion 6a may have a diameter of about 0.008 inches or more (0.2032 mm or more). Other thicknesses are possible. The thickness of the outer conductors and dielectric material in each portion of the cable may be the same or different from each other as required.

Figure 2A:
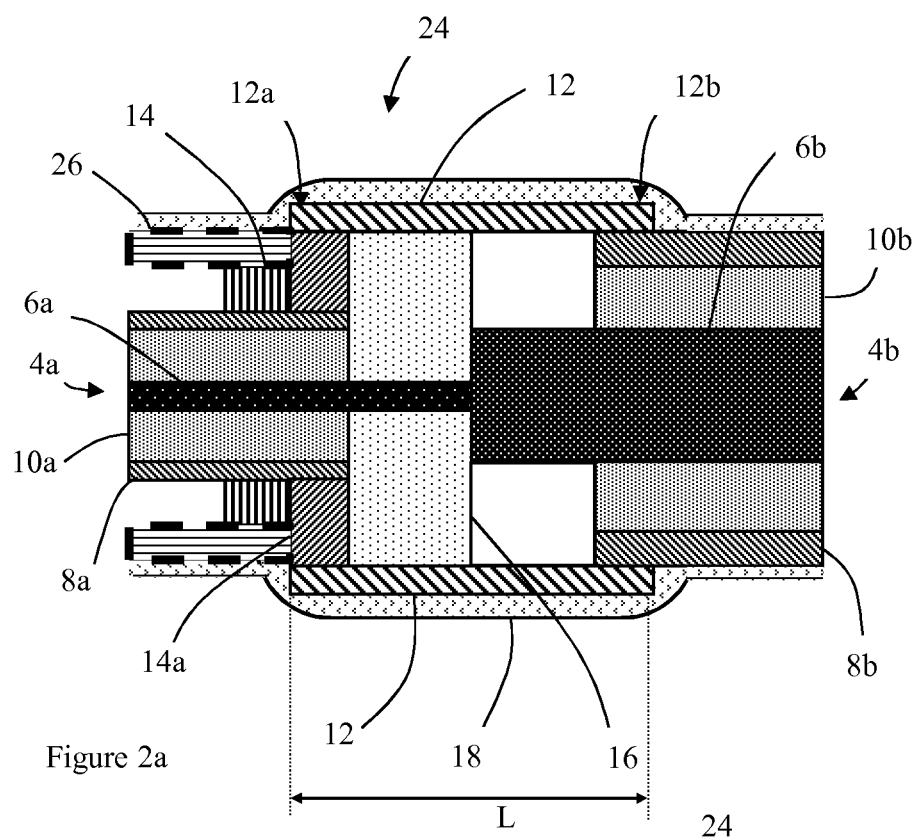
FIG. 2a shows a cross section view of a connector arranged to connect the distal and proximal portions of a feeding cable according to an embodiment.

The ablation probe 1 further comprises a connector 24 arranged to mechanically and electrically splice or couple the distal portion 4a of the feeding cable 4 to the proximal portion 4b of the feeding cable 4. A close up view of the connector 24 is shown in FIG. 2a, along with the connected ends of the proximal and distal portions of the feeding cable 4. FIG. 2a shows a feeding cable having a distal portion 4a connected to a proximal portion 4b. The distal portion 4a comprises an inner conductor 6a, an outer conductor 8a, and a dielectric material 10a between them. The proximal portion 4b comprises an inner conductor 6b, an outer conductor 8b, and a dielectric material 10b between them.

The connector 24 comprises a joining member 12 arranged to mechanically and electrically couple the distal portion 4a of the feeding cable to the proximal portion 4b of the feeding cable. The joining member 12 comprises a proximal end 12b shaped to receive an end of the proximal portion 4b of the feeding cable and a distal end 12a shaped to receive an end of the distal portion 4a of the feeding cable. This may allow a compact and secure mechanical and electrical connection to be formed between the portions of the feeding cable. The joining member may provide a short connector between the portions of the feeding cable. This may improve the flexibility of the ablation probe so that it can be inserted through a working channel. A long rigid section may not otherwise be able to navigate a tortuous path required for delivery to a target site within the body. In one embodiment, the length of the joining member 12 may be in a range between 5 and 15 mm (inclusive). This may provide a suitable level of flexibility. The length (labelled L in FIGS. 2 and 3) may be measured from the most distal to the most proximal end of the joining member 12.

The joining member 12 is generally formed from a generally tubular shaped member. The joining member may form a housing in which the respective ends of the proximal and distal portions 4a, 4b of the feeding cable 4 are received. The respective ends of the portions of the feeding cable therefore extend within or are overlapped with the body of the joining member 12 to help provide a secure connection. The joining member 12 may have a generally circular cross section such that it corresponds to a generally circular cross section of the feeding cable portions. Other cross sectional shapes are however possible. In one embodiment, the tubular member may be formed from a hypotube.

The joining member may be formed from an electrically conducting material to provide an electrical connection between the outer conductors 8a, 8b of the feeding cable 4. The joining member may preferably be made from stainless steel. In other embodiments, the joining member may be formed from any other suitable material such as brass or copper. In yet other embodiments, the joining member 12 may be formed from a flexible metal alloy. In one preferred embodiment, the joining member 12 may be formed from Nitinol.

The inner conductors 6a, 6b of each portion of the feeding cable may be electrically coupled within the body or housing of the connector 24 by a welded joint (for example by laser welding). This may provide a strong and secure connection. The welded joint may be formed by laser welding the ends of the inner conductors together. In other embodiments, the coupling between the inner conductors 6a, 6b may be formed by soldering or any other suitable method such as crimping, or other welding technique.

As described in connection with other embodiments below, the ablation probe may comprise a tube 26 arranged to house at least part of the distal portion 4a of the feeding cable (i.e. part of the distal portion that does not extend into the joining member). A portion of the connector 24 may be arranged to extend within the tube 26 to form a mechanical coupling between them. As can be seen in FIG. 2a, the joining member 12 may comprise a step portion 14 arranged to extend within the tube 26 to provide a mechanical coupling between the joining member 12 and the tube 26. This may reinforce the joint between the portions of the feeding cable. The step portion 14 may further act to space apart the tube 26 and the distal portion 4a of the feeding cable.

The connector 24 may further comprise a dielectric member 16, wherein the dielectric member is arranged to at least partly fill a region between an inner conductor of the proximal and/or distal portion of the feeding cable and the respective outer conductor of the proximal and/or distal portion of the feeding cable. The dielectric member 16 may fill all of the region between the inner conductor of the distal portion, the inner conductor of the proximal portion, the outer conductor of the distal portion and the outer conductor of the proximal portion. In the embodiment shown in FIG.

2a, the dielectric member 16 completely fills the region between the inner conductor 6a and outer conductor 8a of the distal portion 4a. In other embodiments, only part of this region may be filled by the dielectric member 16. In yet other embodiments, the region between the inner and outer conductors (of either or both the distal and proximal feeding cable portions) may be filled with air rather than the dielectric member 16 as will be described in more detail later. The connector 24 may therefore comprise a cavity which is at least partly filled by the dielectric member 16. The dielectric member may surround either or both of the inner conductor of the proximal or distal portions of the feeding cable (or part thereof) within the cavity. The dielectric member 16 may extend all of the way between the inner conductor of one of the cable portions and the inner surface of the joining member 12 as shown in FIG. 2a, or part of the way between them.

In one embodiment, the dielectric member 16 may be arranged to space apart the inner conductor of the proximal and/or distal portions of the feeding cable and an inner surface of the joining member. The dielectric member is therefore arranged to maintain a constant separation (e.g. radial distance) between the inner surface of the joining member 12 and the inner conductors of the feeding cable that extend within it. The dielectric member 16 is arranged to maintain constant separation of the joining member and inner conductors when the connector is bent during use (which may not necessarily be a constant separation along the length of the joining member where a tapered inner wall profile is used). This may help provide constant impedance when the connector is bent during use.

Figure 2B:
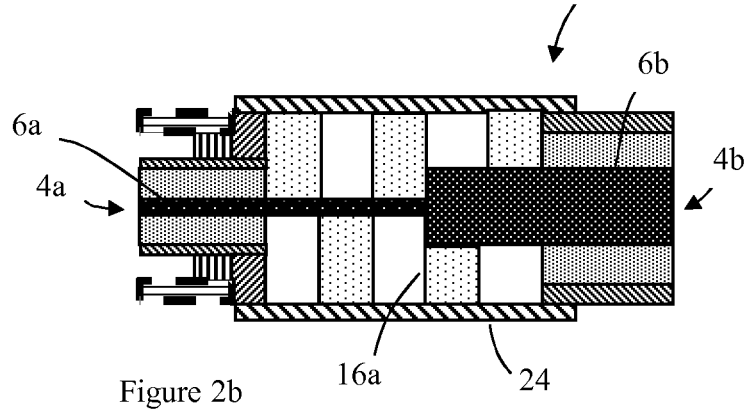
FIG. 2b shows a cross section view of a connector arranged to connect the distal and proximal portions of a feeding cable according to an embodiment having a spiral shaped dielectric element.

In one embodiment, the dielectric member 16 may comprise a spiral element 16a. The spiral element may form a helical shape around a longitudinal axis of the inner conductor of the proximal and/or distal portion of the feeding cable. The spiral shape may help to aid flexibility, whilst also maintaining constant impedance and low electrical losses. An example of a spiral element surrounding the inner conductors of the feeding cables within the cavity inside the joining member is illustrated in FIG. 2b, which shows the turns of the spiral element 16a in cross section.

The connector 24 may further comprise a sealing member 18. The sealing member is arranged to at least partially surround a connection region between the connector and either of the distal portion and proximal portions 4a, 4b of the feeding cable. As can be seen in FIG. 2a, the sealing member may comprise a sealing layer disposed over the joining member 12 and one or both of the proximal portion and distal portion of the feeding cable to seal the connection between them. The sealing member 18 may form a water resistant jacket or skin to prevent water ingress into the connector. The sealing member 18 may be formed from a thin-film or coating. In one embodiment, the sealing member 18 is formed from a polymer, and may be applied by dipping the connector assembly into a polymer dip.

In the embodiment shown in FIG. 2a, the proximal end 12b of the joining member is arranged to fit around the outer conductor 8b of the proximal portion 4a of the feeding cable 4. An inner surface of the joining member 12 therefore contacts an outer surface of the outer conductor 8b of the proximal portion of the feeding cable. This may help form a secure coupling between them. The contact been the joining member 12 and the outer conductor 8b may form an electrical connection between them. The outer conductor 8b and the joining member 12 may be connected by a welded joint. The welded joint may be formed by laser welding. This may provide an electrically and mechanically strong coupling that may prevent coolant ingress. In other embodiments, other welding techniques may be used. In yet other embodiments, other types of bond may be formed between the joining member 12 and the outer conductor 8b.

The distal end 12a of the joining member 12 may be arranged to fit around the proximal end of the distal portion 4a of the feeding cable 4. The joining member 12 may therefore overlap with the proximal end of the distal portion 4a, and may preferably be connected to it by a welded joint, preferably laser welded, to form a secure joint. In other embodiments, the connection may be by soldering, crimping or other suitable technique. The distal end 12a of the joining member 12 may be electrically connected to the outer conductor 8a of the distal portion 4a of the feeding cable to provide an electrical connection between the sections of the feeding cable.

Referring again to FIG. 2a, the joining member comprises a distal aperture adapted to receive the respective end of the distal portion 4a of the feeding cable, and a proximal aperture adapted to receive the respective end of the proximal portion 4b of the feeding cable. The distal aperture is smaller in size compared to the proximal aperture so that it corresponds to the smaller size of the distal portion 4a of the feeding cable 4 compared to the proximal portion 4b.

In the embodiment shown in FIG. 2a, the outer surface of the proximal end 12b of the joining member 12 has the same cross sectional size as the outer surface of the distal end 12a of the joining member 12. In other words, the cross sectional size or outer diameter of the joining member 12 does not change along its length from its distal to proximal ends. A reducer portion 14a may be provided to provide a reduced aperture size to receive the end of the distal portion 4a of the feeding cable 4.

Other embodiments of the connector 24 are illustrated in FIGS. 3 to 7. FIGS. 3 to 7 each show an ablation probe 1 corresponding to that of FIG. 1. Corresponding reference numerals have been used for common features to aid clarity. Any feature described in connection with one of the embodiments shown in one of FIGS. 2 to 7 can be used in combination with another of those embodiments, or any other embodiment of the ablation probe disclosed herein.

Figure 3:
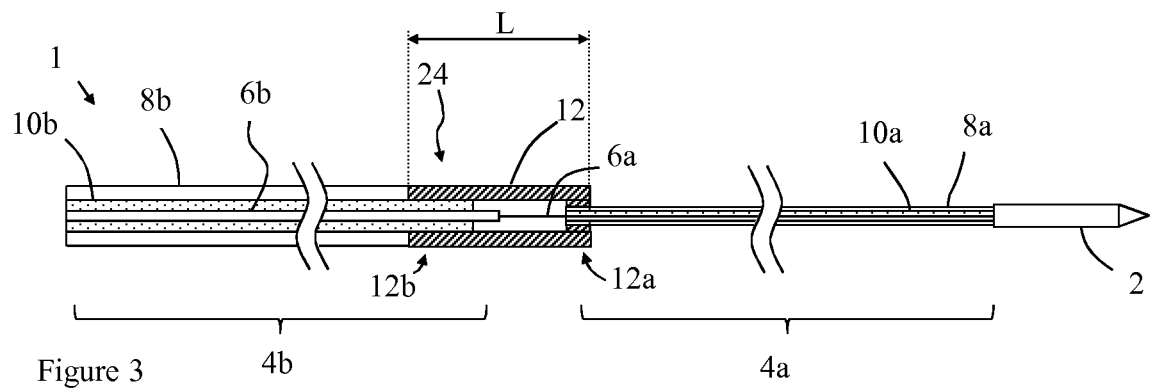
FIG. 3 shows a cross section view of an ablation probe comprising a connector according to another embodiment.

FIG. 3 shows an alternative coupling between the joining member 12 and the proximal portion 4b of the feeding cable. In this embodiment, the proximal end 12b of the joining member 12 is arranged to fit around an exposed portion of the dielectric 10b of the proximal portion 4b of the feeding cable 4. The exposed portion of the dielectric 10b may extend distally from a distal end of the outer conductor 8b and may be formed by stripping an end portion of the outer conductor away to expose part of the dielectric material beneath it.

The joining member 12 may fit around the dielectric 10b so that an outer surface of the joining member 12 is flush with an outer surface of the outer conductor 8b of the proximal portion of the feeding cable. As can be seen in FIG. 3, the outer cross sectional size (e.g. outer diameter) of the joining member 12 adjacent to the outer conductor 8b may be equal to the combined cross sectional size of the inner conductor 8b, dielectric 10b and outer conductor 8b of the feeding cable 4b adjacent to the joining member. This means that the outer surface of the joining member 12 is flush with the outer conductor 8b. Alternatively, the thickness of a wall of the joining member 12 may be equal to the thickness of the outer conductor 8b so that a flush connection is formed. The flush connection may provide a smooth joint between the joining member 12 and the proximal portion of the feeding cable 4a, and may reduce the overall cross section of the ablation probe 1. The joining member may be connected to the outer conductor 8b by a welded joint (e.g. a laser welded joint) as described above. Other connections between the joining member 12 and the outer conductor 8b and/or the dielectric 10b may be used.

Figure 4:
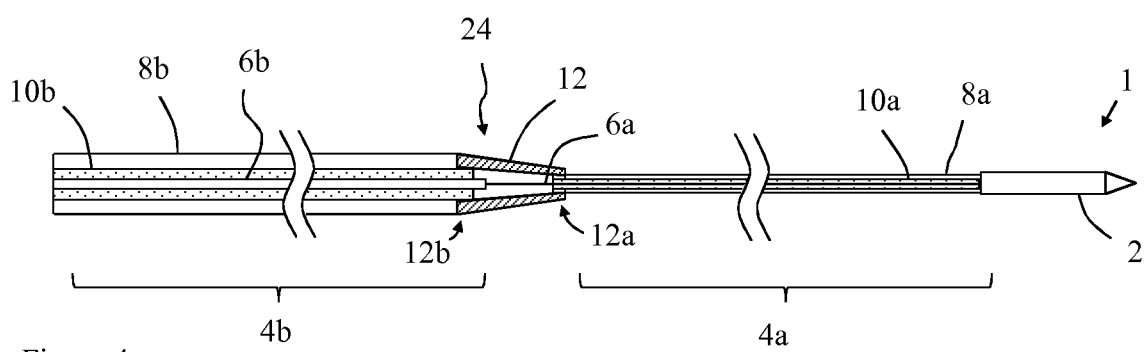
FIG. 4 shows a cross section view of an ablation probe comprising a connector according to another embodiment.
Figure 5:
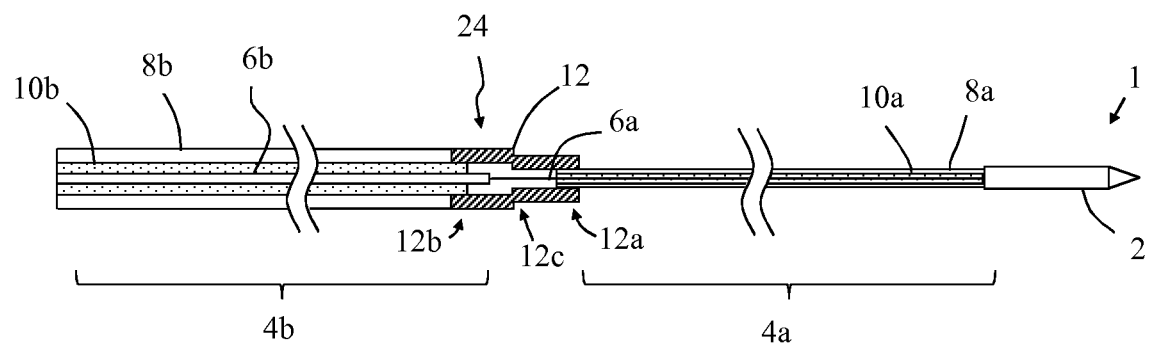
FIG. 5 shows a cross section view of an ablation probe comprising a connector according to another embodiment.

In some embodiments, the outer surface of the proximal end 12b of the joining member 12 may have a greater cross sectional size compared to the outer surface of the distal end 12a of the joining member 12. In other words, the overall cross sectional size or outer diameter of the joining member 12 may reduce along its length between its distal and proximal ends 12a, 12b. An example of this is shown in FIGS. 4 and 5. FIG. 4 illustrates an embodiment in which the outer surface of the joining member 12 comprises a tapered portion extending between its proximal end 12b and its distal end 12a. The tapered outer cross-section may provide a smooth transition from the larger proximal portion 4b of the feeding cable to the smaller distal portion 4a. FIG. 4 shows the tapered portion extending along the whole length of the joining member 12. In other embodiments, only part of the length of the joining member may be tapered.

FIG. 5 illustrates an embodiment in which the outer surface of the joining member 112 comprises a stepped portion 12c disposed at a point along the length of the joining member 12 between its proximal end 12b and its distal end 12a. The stepped portion 12c is arranged to provide a step down in cross sectional size (e.g. outer diameter) of the joining member 12 between its distal and proximal ends 12a, 12b. Although FIG. 5 shows a single stepped portion 12c, one or more stepped portions may be provided at suitable points along the length of the joining member 12. In other embodiments, the stepped portion 12c of FIG. 5 and the tapered portion of FIG. 4 may both be provided.

As illustrated in FIGS. 4 and 5, an inner surface of the proximal end 12b of the joining member 12 may have a greater cross sectional size compared to an inner surface of the distal end 12a of the joining member 12. The inner surface of the joining member may comprise a tapered portion extending at least partly between its proximal and distal ends 12a, 12b as shown in FIG. 4. This may provide a reduction of the inner surface cross sectional size between its distal and proximal ends 12a, 12b, and may correspond to the tapered shape of the outer surface. In the embodiment shown in FIG. 5, the inner surface of the joining member 12 comprises a stepped portion disposed between its proximal end 12b and its distal end 12b to provide a step down in cross sectional size. The stepped portion of the inner surface may correspond to the stepped portion of the outer surface. The tapered or stepped portions provided on the inner surface of the joining member 12 may improve impedance matching (e.g. may help provide a 50 Ohm impedance match). In the described embodiments, the inner surface stepped portion is combined with an outer surface stepped portion, and the inner surface tapered portion is combined with an outer surface tapered portion. In other embodiments, a stepped inner surface may be combined with a tapered outer surface, or vice versa. The shape of the tapered portions and stepped portions of the inner and outer surfaces shown in FIGS. 4 and 5 are examples only, with other shapes being possible. The stepped or tapered portions may, for example, have curved rather than straight profiles as shown.

Figure 6:
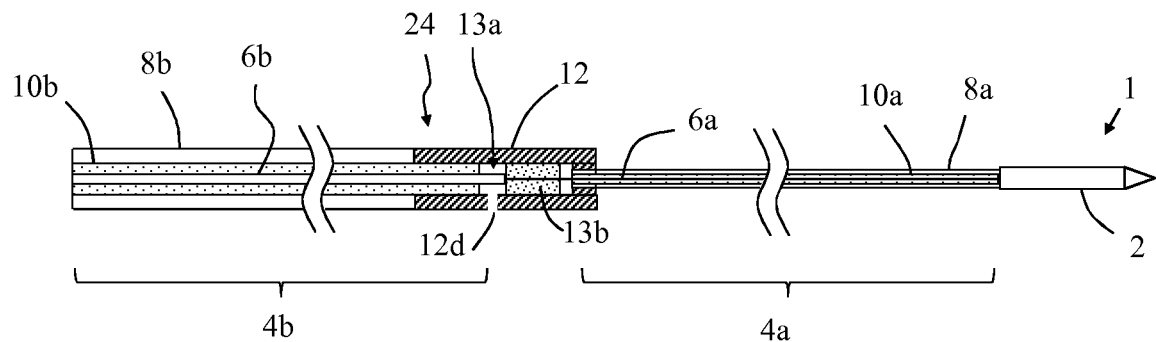
FIG. 6 shows a cross section view of an ablation probe comprising a connector according to another embodiment.

In some embodiments, at least part of the joining member is air filled. An example of this is shown in FIG. 6. The joining member 12 may define a cavity 13a in which the inner conductors 6a, 6b of the feeding cable extend and are joined together. Some, or all, of the cavity 13a may be air filled. By filling at least part of the cavity with air the overall size of the connector 24 may be reduced and help to provide an overall low profile. This is because air has a relatively low dielectric constant, meaning a large volume of other dielectric constant is not required. In some embodiments, the cavity 13a is entirely air filled, with no other dielectric material (e.g. no solid dielectric or potting agent) provided.

Figure 7:
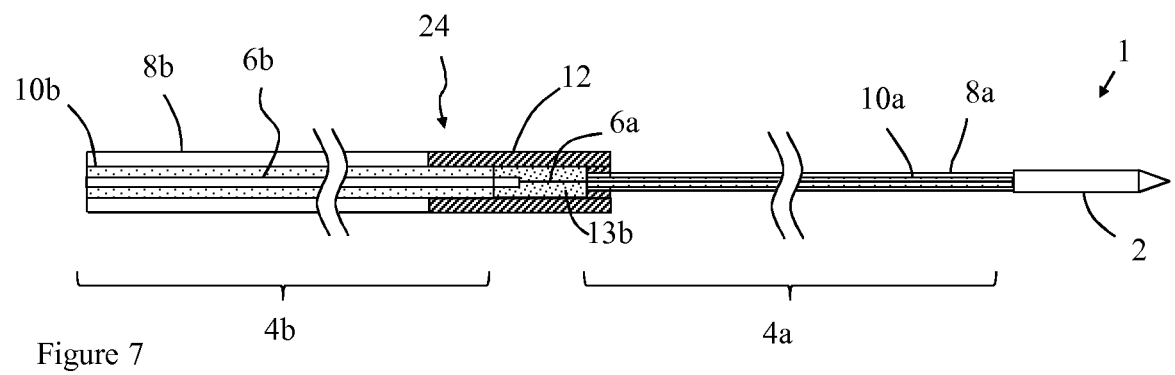
FIG. 7 shows a cross section view of an ablation probe comprising a connector according to another embodiment.

At least part of the joining member may be filled with a potting agent 13b. As illustrated in FIG. 6, part of the cavity 13a may be filled with the potting agent so that its surrounds one or both of the inner conductors 6a, 6b of the feeding cable 4. The potting agent 13b may comprise any suitable potting agent or compound known in the art. It may, for example, comprise an epoxy with a low dielectric value which allows the diameter of the connector to be minimised, and may provide improved structural strength. In some embodiments, all of the cavity 13a may be filled with potting agent 13b as illustrated in FIG. 7. In yet other embodiments, all of the cavity may be air filled, or filled with a combination of air, potting agent and any other suitable dielectric material as discussed in connection with FIG. 2a.

Referring again to FIG. 6, the joining member 12 may further comprises a bleed hole 12d. The bleed hole 12d may comprise a through hole extending through the body or wall of the joining member 12. The bleed hole 12d may be configured to allow the flow of potting agent 13b into or out of the cavity 13a within the joining member. This may allow air to escape during manufacture to avoid undesired air pockets being formed.

Figure 8:
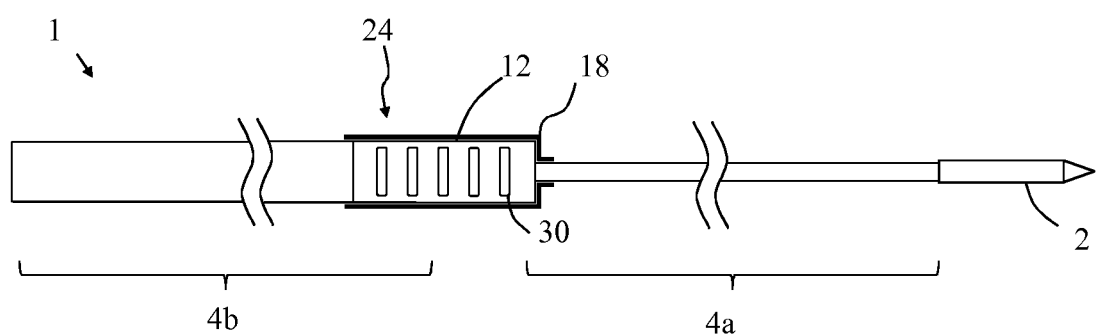
FIG. 8 shows a cut away side view of an ablation probe comprising a connector according to another embodiment.

In other embodiments, the joining member 12 comprises one or more weakened portions. The weakened portions are arranged to increase the flexibility of the joining member 12 so that the ablation probe 1 can be used effectively with an endoscope type delivery device. An example of such an embodiment is illustrated in FIG. 8. In this embodiment, the joining member 12 comprises a plurality of slots 30 extending through the body of the joining member 12 forming a series of weakened portions. In other embodiments, only a single slot may be provided. The slots may be any suitable shape or pattern to provide the desired level of flexibility. In the described embodiment, the slots 30 extend through the body of the joining member 12. In other embodiments, the weakened portions may be formed by slots or cuts in the surface of the joining member 12. In such an embodiment, the slots or cuts do not extend all the way through its body. The weakened portions may be formed by laser cutting the joining member 12.

In the embodiment of FIG. 8 the connector comprises a sealing member 18 described elsewhere herein. The sealing member 18 extends over the joining member in order to prevent water ingress through the slots forming the weakened portions.

Figure 9:
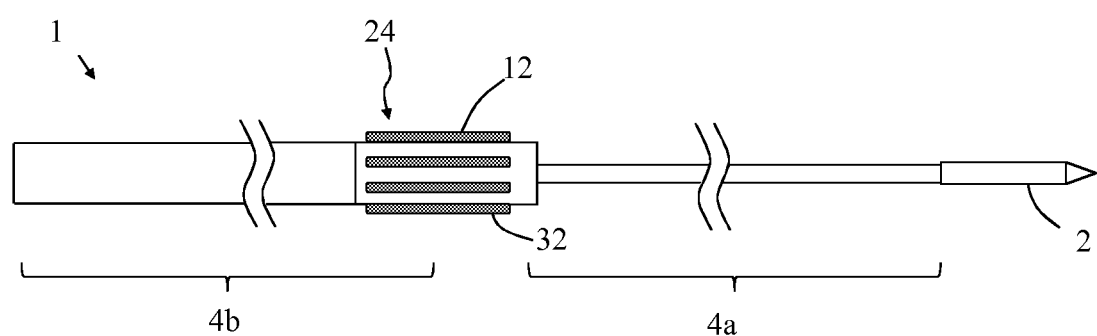
FIG. 9 shows a side view of an ablation probe comprising a connector according to another embodiment.

FIG. 9 illustrates an embodiment in which the joining member 12 has a non-circular outer profile. In the embodiment shown in FIG. 9, the joining member 12 comprises a heat transfer structure. The heat transfer structure is formed from a plurality of protrusions (e.g. fins) extending from the outer surface of the joining member (four of which are visible in FIG. 9). The protrusions are adapted to increase the surface area of the joining member and aid heat transfer from the joining member 12 to its surroundings. FIG. 9 shows only one example, in other embodiments other numbers of protrusions, or shapes of protrusions, may be provided.

The connector 24 described above may be used in any ablation probe having a feeding cable in which distal and proximal portions are coupled together, examples of which are described in more below. The connector may, for example, be used in an ablation probe according to those disclosed in the applicant's previous applications: European application No. EP17164403.2 and International application No. PCT/EP2018/058252 (the contents of which are hereby incorporated by reference in their entirety), which disclose an ablation probe having a coolant flow path defined partly by a deformable member. The skilled person will however understand that the connector 24 is not limited to use with such ablation probes, and can be used with ablation probes with and without coolant flow paths, and with or without deformable members forming a coolant flow path.

Figure 10A:
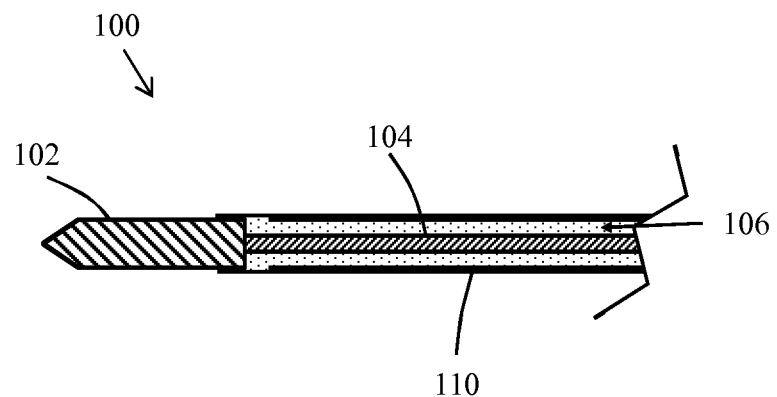
FIGS. 10a and 10b show a schematic view of part of an ablation probe according to an embodiment.
Figure 10B:
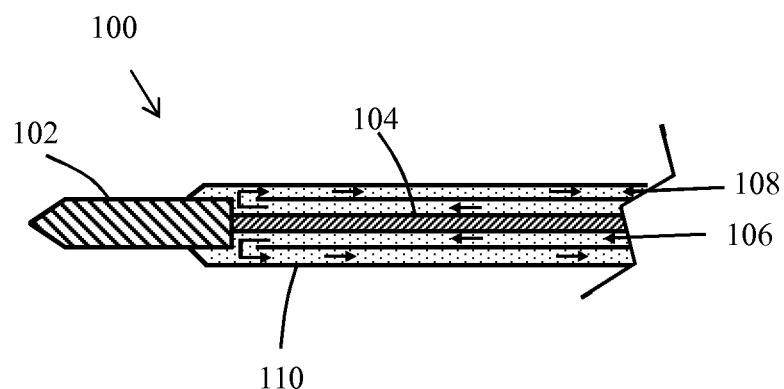

An example of an ablation probe 100 with which the connector may be used in shown in FIGS. 10a and 10b. The ablation probe 100 comprises an applicator 102 and a feeding cable 104 corresponding to those described in connection with FIG. 1. Corresponding reference numbers have been used in FIGS. 10a and 10b for feature common with those described in connection with FIGS. 1 to 9.

The ablation probe 100 further comprises a first coolant path. In the described embodiment, the first coolant path is a coolant delivery path 106 via which coolant is able to flow towards the applicator 102. For example, the coolant delivery path 106 may deliver a flow of coolant towards the distal end of the ablation probe 100 from a coolant supply means (not shown in the Figures) coupled to the coolant delivery path 106 at the proximal end of the ablation probe 100. The flow of coolant may help control the temperature of the ablation probe 100 during use. This may allow energy to be delivered to the surrounding tissue for an extended period of time without the ablation probe 100 overheating and being damaged, or causing injury to healthy tissue. The coolant delivery path may be formed by one or more coolant channels as will be described later. The coolant may be a fluid, and may be water, saline solution, a cryogenic gas or any other suitable coolant known in the art.

The ablation probe 100 further comprises a second coolant path. In the described embodiment, the second coolant path is a coolant return path 108 via which coolant can return from the applicator. The coolant return path 108 may therefore return the supply of coolant from the distal end of the ablation probe 100 to the proximal end. The ablation probe 100 further comprises a deformable member 110 which is arranged to move between an insertion configuration (shown in FIG. 10a) in which insertion of the ablation probe 100 is facilitated and a deployed configuration (shown in FIG. 10b). When in the deployed configuration, the coolant return path 108 is provided by the deformable member 110. In some embodiments, no coolant return path may be provided when the deformable member is in the insertion configuration. This may allow the profile of the ablation probe to be minimised. In other embodiments, the return path may not be completely absent when the deformable member is in the insertion configuration. The insertion configuration therefore provides a configuration in which the ablation probe 100 may be suitable for delivery to the desired location within the body. The insertion configuration may, for example, correspond to a suitable size and/or shape adapted to allow insertion with reduced risk of undesired tissue damage. When in the insertion configuration, the ablation probe 100 may, for example, have a low profile (e.g. small cross sectional size) for ease of insertion through tissue without causing injury or insertion through the working channel of an endoscope.

In other embodiments, the first coolant path may act as a coolant return path. In this embodiment, the first coolant path is arranged to carry a flow of coolant away from the applicator. In this embodiment, the second coolant path may act as a coolant delivery path arranged to carry a flow of coolant towards the applicator. A combination of the first and second coolant paths may therefore form a coolant circuit arranged to deliver a flow of coolant to and away from the applicator, where the coolant can flow in either direction along each of the first and second coolant paths. In the embodiment shown in the figures, the first coolant path acting as the coolant delivery path may allow a flow of colder coolant close to the feeding cable. This may aid cooling of the ablation probe as a significant amount of heat may be generated in the feeding cable. In other embodiments, where the second coolant path acts as the coolant delivery path, colder coolant may be delivered to the applicator first to aid cooling of the applicator.

The ablation probe 100 may therefore be delivered to the desired location whilst the deformable member 110 is in the insertion configuration. Once at the desired location, the deformable member 110 may be moved to the deployed configuration to allow flow of the coolant away from the applicator 102. The coolant can then flow via the coolant delivery and return paths to cool the ablation probe 100 during use. The deformable member 110 therefore is able to provide an insertion configuration suitable for delivery to the ablation site when the coolant flow is not required. Once the ablation probe is in position, the deformable member 110 may be moved to a configuration suitable to provide a flow of coolant as required during delivery of energy from the applicator 102. When in the deformable member is in the insertion configuration the overall diameter of the ablation probe may be between about 13 to about 25 gauge (approximately 2.5 to 0.5 mm). This may allow easy insertion.

As can be seen in FIGS. 10a and 10b, the coolant return path 110 may be provided only by the deformable member along at least a portion of a length of the ablation probe 100. For example, along at least part of the length of the ablation probe 100, no other channels or conduits to carry returning coolant may be provided in addition to the coolant return path 108 formed by the deformable member 110. This may allow the ablation probe 100 to have a small cross sectional size when the deformable member is in the insertion configuration. Any additional coolant return paths would require additional space within the body of the ablation probe 100 and so would not provide a low profile.

In the embodiment of FIGS. 10a and 10b, the deformable member 110 is fluidly connected to a distal end of the coolant delivery path 106 (e.g. the distal end of the coolant delivery path may be joined to the distal end of the fluid return path to form a single path along which coolant may flow towards and then away from the applicator (in either direction)). The coolant delivery path 106 therefore runs along the inside of the coolant return path 108 when the deformable member 110 is in the deployed configuration. This arrangement allows the overall size of the ablation probe 100 to be reduced when the deformable member 110 is in the insertion configuration.

An example embodiment of an ablation probe 200 according to this disclosure is shown in more detail in FIGS. 11 to 17. The embodiment shown in the Figures is only one such example.

As can be seen in FIG. 11, in this embodiment, the ablation probe 200 generally comprises two portions: a needle portion 212 and a catheter portion 214. The needle portion 212 may be arranged at the distal end of the ablation probe 200 and is adapted to be inserted into tissue during use to reach the desired ablation location. The catheter portion 214 may be provided at the proximal end of the ablation probe 200 and is arranged to supply electromagnetic energy and a flow of coolant to and from the needle portion 212. In the embodiment shown in the Figures, the ablation probe 200 further comprises a handle portion 216 via which the ablation probe may be manipulated and positioned during use. The catheter portion may have an extended length and flexibility for endoscopic use as shown in FIG. 11. In other non-claimed embodiments, a shorter, more rigid catheter portion may be provided for percutaneous use.

In some embodiments, the needle portion may form a small part of the overall length of the ablation probe. For example, the needle portion may be 5 mm to 2000 mm in length, and preferably may be around 70 mm in length. The length of the needle portion may be chosen according to the anatomy to be accessed. For example, the needle portion may be approximately between 10 and 100 mm long for delivery of therapy to organs including the pancreas, or lung, or longer (for example 100-400 mm in length) for delivery of therapy percutaneously. A longer length of needle portion may be more suitable for accessing parts of the lung, for example. The catheter portion may be around 1000 mm to 2000 mm in length, and preferably around 1400 mm in length. The length of the catheter portion may be chosen according to the position of the ablation site which must be reached. In other embodiments, the needle portion of the ablation probe (e.g. that having the deformable member) may form a greater proportion of the length of the ablation probe. In some embodiments, the entire length of the ablation probe may be formed by the needle portion. In such an embodiment, the deformable member may extend along the majority or all of the length of the ablation probe. In such an embodiment, the catheter portion may not be required. For example, if the ablation probe is to be used percutaneously the catheter portion may be shorter than for endoscopic use, or may not be required.

Figure 12:
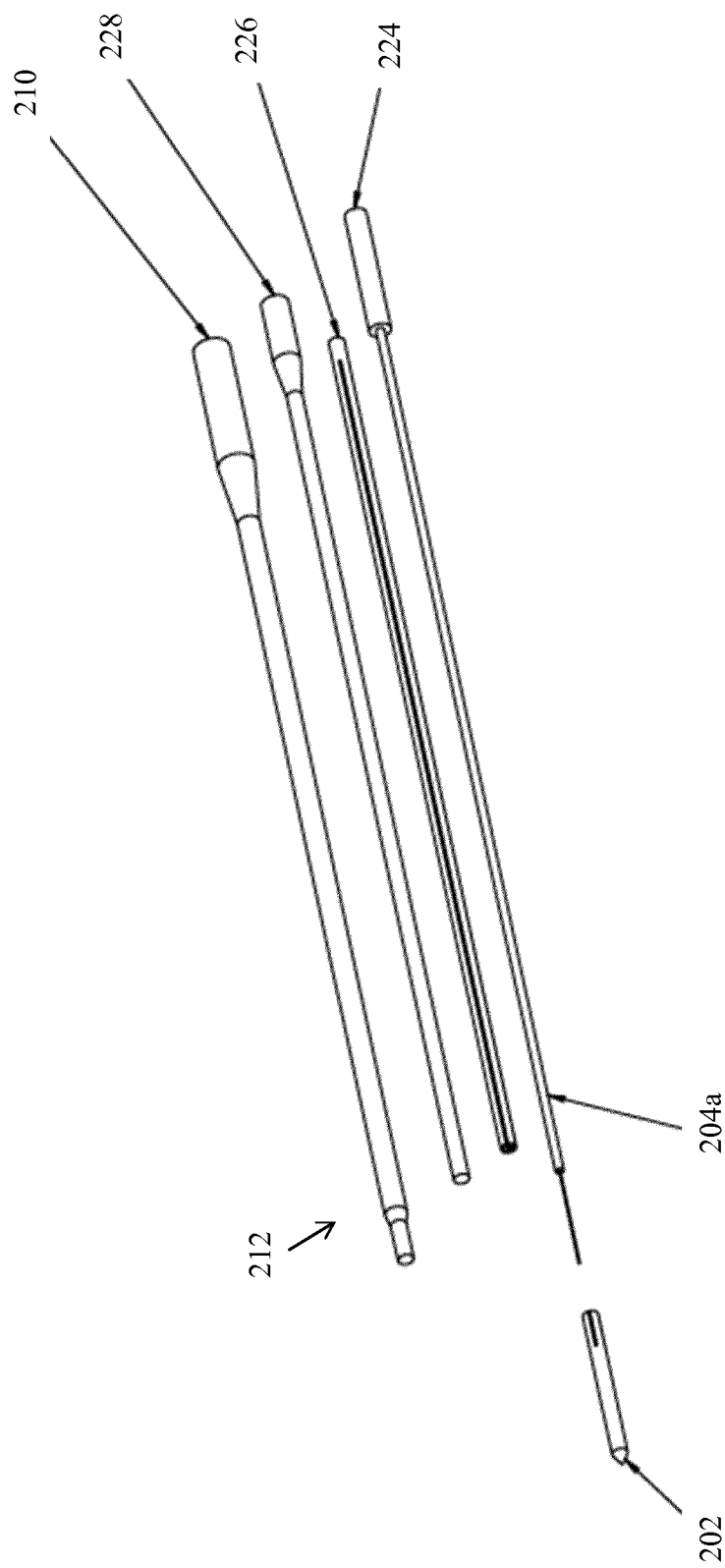
FIG. 12 shows an exploded view of a needle portion of the ablation probe shown in FIG. 11.

An exploded view of the needle portion is shown in FIG. 12. The needle portion 212 may comprise a deformable member 210, an applicator 202, a distal portion of the feeding cable 204a and a distal portion of the coolant delivery path. An exploded view of the catheter portion is shown in FIG. 13. In this embodiment, the catheter portion 214 may comprise a proximal portion of the feeding cable 204b, a proximal portion of the coolant delivery path, and a coolant return conduit (which may be non-deformable). The proximal portion of the coolant delivery path may be formed by a space between a tube 218 housing the proximal portion of the feeding cable 204b and a surrounding coolant delivery tube 220. The coolant return path may be formed by a space between the coolant delivery tube 220 and a surrounding coolant return tube 222. In other embodiments, any other suitable arrangement of channels or conduits may be provided to form the coolant return and coolant delivery paths within the catheter portion 214.

The greatest cross sectional size of the needle portion may be less than the greatest cross sectional size of the catheter portion. In other words, the cross section size (e.g. diameter) of the needle portion at its largest point may be less that the cross sectional size (e.g. diameter) of the catheter portion at its greatest point. This may allow the needle portion to access an ablation site whilst reducing any potential for tissue damage. The catheter portion on the other hand may be sized to fit through the working channel of the device with which it is used.

Examples of suitable arrangements of channels forming the coolant return and coolant delivery paths are shown in the cross sectional views of FIGS. 14a to 14c. In FIG. 14a, the catheter portion comprises two lumens each forming one of the coolant return and coolant delivery paths. In FIG. 14b, the catheter portion comprises four lumens forming the coolant return path and coolant delivery path. Two of the lumens may form the coolant return path, and two of the lumens may form the coolant delivery path. This embodiment may provide better kink resistance and strength. The lumens may not be equally sized as shown in FIGS. 14a and 14b. An example of this is shown in FIG. 14c in which three lumens are provided. A first and second lumen may provide the coolant return and delivery paths, with the third lumen provided to include other components such as a sensor or the like. The third lumen may be small in size compared to the first and second lumens to provide adequate space for the flow of coolant.

In other embodiments, the channels forming the coolant return and coolant delivery paths within the catheter portion may be formed by one or more channels in the outer conductor of the proximal portion of the feeding cable. This may improve flexibility and provide a compact arrangement.

In the described embodiment, the feeding cable is formed by two lengths of cable (the distal portion 204a and the proximal portion 204b) joined at the boundary between the needle portion 212 and the catheter portion 214 (shown in more detail in the close up view of FIG. 15a). The feeding cable may be formed by two lengths of coaxial cable to form an electrical circuit to deliver electromagnetic energy to the applicator 202. In other embodiments a single feeding cable may be used having regions of different thickness to form the distal and proximal portions. In other embodiments, any other suitable conductor may be provided to deliver a supply of suitable electromagnetic energy to the applicator 202. The ablation probe 200 may further comprise a connector 224 arranged to mechanically and electrically splice the distal portion of the feeding cable 204a to the proximal portion of the feeding cable 204b as described above in connection with the embodiments of FIGS. 1 to 9. The connector 224 may connect the different portions of the feeding cable 204a, 204b while maintaining an effective impedance match, minimising electrical losses and ensuring a compact configuration of the ablation probe 200.

In the described embodiment, the distal portion of the feeding cable 204a has a corresponding distal cross sectional size, and a proximal portion of the feeding cable 204b has a corresponding proximal cross sectional size, wherein the distal cross sectional size is less than the proximal cross sectional size. The size (e.g. diameter) of the conductor is therefore optimised based on its position within the ablation probe 200. The cross sectional sizes may be chosen to optimise (e.g. maximise) the feeding cable power handling, while also reducing electrical losses and optimising the mechanical strength of the ablation probe 200. In other words, the length of the smaller cross section portion of the feeding cable is minimised by connecting it to a larger cross section feeding cable (e.g. a more efficient cable) for the portion of the ablation probe 200 outside of the needle portion 212. This part of the ablation probe 200 does not need to be inserted into tissue so a small profile is not as important. The cross section of the feeding cable in the catheter portion 212 is therefore increased to reduce power loss where a small cross section is less important.

The needle portion of the ablation probe may therefore have a smaller overall cross sectional size compared to the catheter portion. The needle portion is therefore optimised for insertion into tissue, whilst the catheter portion is optimised for power delivery over the long length of a device working channel through which it is inserted. In use, only the needle portion may protrude from the working channel through which the ablation probe is inserted. It is therefore important for the needle portion to have a relatively small cross sectional size to reduce tissue damage. For the catheter portion a relatively larger cross sectional size can be used. Compared to the needle portion, the catheter portion is instead optimised for power delivery along the length of the working channel. In one example, the needle portion, when the deformable member is in the insertion configuration, may have an overall diameter of 1 mm at its largest point. The catheter portion may have an overall diameter of 3 mm at its largest point.

In other embodiments, the cross sectional size of the distal and proximal portions of the feeding cable may be the same. In this case, a reduction in overall size of the needle portion compared to the catheter portion may still be provided by the use of the deformable member.

The needle portion 212 may further comprise a tube 226 (e.g. a hypotube) arranged to house the distal portion of the feeding cable 204a. The tube 226 may be formed from a metal material which has sufficient rigidity to allow the needle portion 212 to be inserted into tissue. In other embodiments, the tube 226 may be formed from any other suitable material and may be formed from a superelastic material, for example Nitinol.

In other embodiments, the tube 226 may be formed form an elastic material (and not specifically a superelastic material). By forming the tube from an elastic (or superelastic) material it may withstand permanent deformation after being delivered through the tortuous path of a working channel. As the ablation probe extends from the working channel it may consequently follow a straight path, rather than following a curved path caused by the material being deformed by the shape of the working channel. This may help to more easily guide the distal tip of the ablation probe to the desired position.

An example of this is shown in FIGS. 15b and 15c. FIG. 15b shows an example of an ablation probe 200 having a tube formed from an elastic material extending from the end of the working channel 201 through which it has been inserted. The portion of the ablation probe extending from the working channel can be seen to follow a straight path. FIG. 15c shows an example of an ablation probe with a non-elastic tube. This figure illustrates how the portion of such an ablation probe extending from the working channel 201 tends to follow a curved path.

In some embodiments, the tube may be formed from an elastic (or superelastic) electrically conducting material. This may allow the tube to form part of a choke. The tube may be formed from a solid material or a mesh material as appropriate to allow the required elasticity, for example a braid or coil reinforced polymer tube.

In one embodiment, the coolant delivery path is provided by a channel formed between the feeding cable and inside wall of the tube 226. For example, clearance between the feeding cable and the inside wall of the tube 226 may provide space for coolant to flow. In other embodiments, slots may be cut into the inside wall of the tube 226 to provide a space through which coolant can flow. The amount of clearance may be specified to ensure an adequate flow of cooling is achieved while maximising the power carrying capacity of the feeding cable.

In the embodiment shown in the Figures, the coolant delivery path comprises one or more coolant channels formed in the body of the tube 226. The coolant therefore may partly surround the feeding cable to aid cooling. The width and number of the channels may be chosen to optimise (e.g. maximise) the mechanical strength of the ablation probe 100 and the performance of the cooling.

The one or more channels may be cut into the wall of tube 226 to allow cooling fluid to flow adjacent to the distal portion of the feeding cable 204a. In the described embodiment, the one or more channels may be formed by one or more slots formed in the outer surface of the tube 226. In this embodiment, the ablation probe 200 may further comprise a membrane 228 disposed around the tube 226. The membrane 228 may be arranged to separate the coolant delivery path from the coolant return path (e.g. it forms a boundary between them). In some embodiments, the one or more channels may extend distally past a distal end of the membrane 228 so that coolant can flow from the one or more channels into the deformable member 210.

In other embodiments, one or more apertures may be provided in the membrane 228 to fluidly connect the one or more channels with the deformable member 210. The membrane 228 may be formed from a thin layer of material (for example a polymer heat shrink) located over the tube 226 to form an enclosed conduit for the cooling fluid. In other embodiments, the channels may be formed within the wall of the tube 226, in which case the membrane 228 may not be required.

In other embodiments (not shown in the Figures), the distal portion of the feeding cable 204a may comprise an inner conductor arranged to transmit a signal to the applicator 202 and an outer conductor arranged to shield the inner conductor (e.g. it may be a coaxial cable). The coolant delivery path may comprise one or more coolant channels formed in the outer conductor. The coolant channels may, for example, be formed by one or more slots in an outer surface of the outer conductor. The coolant and the split outer conductor may thus form a mixed media outer conductor arranged to shield the electrically insulating material. A membrane may be formed around the outer conductor to form a conduit for the cooling fluid. In some embodiments, the feeding cable may be formed by a coaxial cable in which the outer conductor is manufactured from a robust material (for example stainless steel) to form a ridged body of the needle portion. In this embodiment, the coolant delivery path may be formed by channels in the outer conductor, rather than in the tube 228. In such an embodiment, the tube may therefore not be required, thus saving space. In other embodiments, the tube may also be provided. The cooling channels may also more effectively cool the feeding cable as well as deliver coolant to the applicator 202. In some embodiments, the one or more channels formed in the outer conductor may be aligned with the central axis of the feeding cable. The width and number of the channels may be chosen to optimise the mechanical strength of the feeding cable and the performance of the cooling, while minimising electrical losses and ensuring impedance matching between portions of the feeding cable having channels in the outer conductor and portions of the feeding cable in which the channels are not present (e.g. in the catheter portion).

The one or more coolant channels described above forming the coolant delivery path may be disposed along a length of the ablation probe as can be seen in the close up view of the tube 226 shown in FIG. 16. In some embodiments, a plurality of channels may be provided such that they are spaced equally around a circumference of the outer conductor or tube 226 housing the feeding cable. In FIG. 16 only one of the channels is visible (labelled 230). In some embodiments, the plurality of channels may comprise four channels spaced equally around the circumference of the outer conductor or tube 226 housing the feeding cable. In other embodiments, other numbers and arrangements of channels may be provided according to the cooling requirements and mechanical strength requirements of the ablation probe.

The inner conductor of the distal portion of the feeding cable 204a is coupled to the applicator 202 as shown in the detailed view of FIG. 17. In this embodiment, a distal end of the distal portion of the feeding cable is connected to a proximal end of the applicator 202. Where the feeding cable is formed from an inner and outer conductor, the inner conductor may be attached to the applicator 202 to ensure efficient transfer of electromagnetic energy to the applicator material. The applicator 202 may be formed from a ceramic material with suitable dielectric properties (for example zirconia) according to the energy it is arranged to apply. An internal bore may be provided in the applicator 202 to receive a portion of the inner conductor to ensure a strong mechanical joint that may also be glued in position. The applicator 202 may further be coupled to the tube 226 housing the feeding cable where it is provided. In such an embodiment, the proximal end of the applicator 202 may be connected to the tube 226 via a bore to receive the tube or a set of interlocking fingers to maximise the mechanical strength of the bond between them. In other embodiments, any other suitable connection means between the tube 226 and the applicator 202, or the distal portion of the feeding cable 204a and the applicator 202 may be provided.

The needle portion further comprises the deformable member 210 as shown in the exploded view of FIG. 12. In the described embodiment, the deformable member 210 is formed by an inflatable member arranged to move between a deflated configuration when the deformable member 210 is in the insertion configuration and an inflated configuration when the deformable member 210 is in the deployed configuration. The inflatable member may thus form a balloon which may be inflated by the flow of coolant (e.g. the inflatable member may inflate due to the pressure of the coolant). In the described embodiment, the inflatable member has an inside diameter that matches the outside diameter of the tube 226 (or the membrane 228 surrounding the tube 228 or the outer conductor or insulating material respectively). The inflating member may inflate to a larger diameter when the cooling system is pressurised. This may therefore form a conduit for the cooling fluid to return from the applicator 202. When moving to the inflated configuration, some, or all, of the inflating member may change shape (e.g. expand) to allow space for the coolant to flow. When the inflation member is deflated, the insertion profile of the ablation probe 200 may be reduced (e.g. minimised) to aid delivery to the target ablation site. When the ablation therapy has been delivered, the inflation member may be deflated so that it returns to its original diameter to facilitate removal.

The deformable member 110 may extend along at least part of the length of the needle portion 212 as shown in the Figures. The deformable member 110 may, for example, extend from at or near the boundary between the needle portion 212 and the catheter portion 214 and end at or near the proximal end of the applicator 202. The coolant may therefore flow through the deformable member 210 along the length of the ablation probe (e.g. a flow of coolant may be provided between an inlet and an outlet of the deformable member, the inlet and outlet being spaced apart along the length of the ablation probe). The deformable member 210 may be fluidly connected to the non-deformable coolant return conduit at a boundary between the needle portion 212 and the catheter portion 214. The coolant may therefore flow through the deformable member 110 (when in the deployed configuration) and then through the non-deformable coolant return conduit in the catheter portion to reach the proximal end of the ablation probe 200.

Various modifications will be apparent to the skilled person without departing form the scope of the claims. Any feature disclosed in connection with one embodiment may be used in combination with the features of another embodiment.

Test Results

The performance of an ablation probe according to the present application has been evaluated by the inventors. An assembly comprising a proximal length of coaxial cable, a distal length of relatively thinner coaxial cable, and a connection formed by a joining member receiving the end of each cable was manufactured and tested. The embodiment tested was similar to that shown in FIG. 3, with the joining member having a slightly larger cross-section than the proximal portion of the feeding cable, and only air filling the cavity inside the joining member. Similar advantageous results would however be expected for the other embodiments described herein.

The electrical losses in the connector were evaluated by subtracting the sum of electrical losses for each individual cable section (i.e. the assembly without the connector) and the electrical losses of the prototyped assembly (i.e. the assembly including the connector) across a frequency bandwidth of 2.4-2.5 GHz.

The electrical losses for the prototyped assembly are shown in Table 1 below and FIG. 18. The prototype shows very low electrical losses in the connector across the frequency bandwidth 2.4-2.5 GHz. At 2.45 GHz, the connector enables a reduction of electrical losses of 31% compared to a coaxial cable section of constant diameter (i.e. the same diameter as the thinner distal portion) and the same length as the tested assembly.

TABLE 1

| Frequency | Losses [dB] |
| --- | --- |
| 2.4 | 0.02 |
| 2.405 | 0.016 |
| 2.41 | 0.022 |
| 2.415 | 0.025 |
| 2.42 | 0.03 |
| 2.425 | 0.037 |
| 2.43 | 0.037 |
| 2.435 | 0.04 |
| 2.44 | 0.04 |
| 2.445 | 0.055 |
| 2.45 | 0.055 |
| 2.455 | 0.065 |
| 2.46 | 0.065 |
| 2.465 | 0.07 |
| 2.47 | 0.075 |
| 2.475 | 0.075 |
| 2.48 | 0.08 |
| 2.485 | 0.085 |
| 2.49 | 0.085 |
| 2.495 | 0.087 |
| 2.5 | 0.087 |

A tensile force test on the joint between inner conductors of the same prototype showed that the strength of the connection between the inner conductors of the two coaxial cables is higher than the strength of the inner conductor of the distal cable portion (i.e. with no joins).

A tensile force test was also carried out on the laser welded joints provided in the test prototype between the outer conductors and the joining member forming the connection. The laser welded connection between the outer conductors and the joining member resulted in a stronger connection compared to the strength of the outer conductor of the distal portion of the feeding cable (i.e. with no welded joint). The connector was therefore found to provide a suitably strong connection between the separate sections of coaxial feeding cable.

The prototyped connector assembly was also tested for water-resistance. In the embodiment being tested, a laser welded joint between the outer conductors of the feeding cables and the joining member of the connector provided the desired sealing. After immersion in water at the pressure of 8 bar for one hour, no water ingress was observed.

The invention claimed is:

1. An ablation probe, comprising:
   an applicator arranged to apply radiation to heat surrounding tissue;
   a feeding cable arranged to supply electromagnetic energy to the applicator, wherein the feeding cable comprises a distal portion and a proximal portion, wherein the distal portion of the feeding cable has a distal cross sectional size and the proximal portion of the feeding cable has a proximal cross sectional size, wherein the distal cross sectional size is less that the proximal cross sectional size; and
   a connector arranged to mechanically and electrically couple the distal portion of the feeding cable to the proximal portion of the feeding cable,
   wherein the connector comprises a joining member comprising a proximal end shaped to receive an end of the proximal portion of the feeding cable and a distal end shaped to receive an end of the distal portion of the feeding cable;
   at least part of the joining member is filled with a potting agent; and
   the joining member further comprises a bleed hole, the bleed hole being configured to allow the flow of potting agent into or out of a cavity within the joining member.

2. An ablation probe according to claim 1, wherein the distal portion of the feeding cable comprises an inner conductor, an outer conductor, and a dielectric between them, and the proximal portion of the feeding cable comprises an inner conductor, an outer conductor and a dielectric between them.

3. An ablation probe according to claim 2, wherein the proximal end of the joining member is arranged to fit around the outer conductor of the proximal portion of the feeding cable.

4. An ablation probe according to claim 2, wherein the proximal end of the joining member is arranged to fit around an exposed portion of the dielectric of the proximal portion of the feeding cable, the exposed portion of the dielectric extending distally from a distal end of the outer conductor.

5. An ablation probe according to claim 4, wherein an outer surface of the joining member is flush with outer surface of the outer conductor of the proximal portion of the feeding cable.

6. An ablation probe according to claim 2, wherein the inner conductors of each portion of the feeding cable are electrically coupled within the body of the connector, and preferably the inner conductors are coupled by a welded joint.

7. An ablation probe according to claim 1, wherein the ablation probe further comprises a tube arranged to house at least part of the distal portion of the feeding cable, and wherein a portion of the joining member is arranged to extend within the tube to form a mechanical coupling between them.

8. An ablation probe according to claim 1, wherein at least part of the joining member is air filled.

9. An ablation probe according to claim 2, wherein the joining member comprises a dielectric member surrounding at least part of the length of the inner conductor of the proximal and/or distal portions of the feeding cable that extend within the joining member.

10. An ablation probe according to claim 9, wherein the dielectric member is arranged to space apart: the inner conductor of the proximal and/or distal portions of the feeding cable; and an inner surface of the joining member.

11. An ablation probe according to claim 9, wherein the dielectric member comprises a spiral element, the spiral element preferably forming a helix around a longitudinal axis of the inner conductor of the proximal and/or distal portion of the feeding cable.

12. An ablation probe according to claim 1, wherein an outer surface of the proximal end of the joining member has a greater cross sectional size compared to an outer surface of the distal end of the joining member, and wherein:
   the outer surface of the joining member comprises a tapered portion extending at least partly between its proximal and distal ends; and/or
   the outer surface of the joining member comprises a stepped portion disposed between its proximal and distal ends.

13. An ablation probe according to claim 1, wherein an inner surface of the proximal end of the joining member has a greater cross sectional size compared to an inner surface of the distal end of the joining member, and wherein:
   the inner surface of the joining member comprises a tapered portion extending at least partly between its proximal and distal ends; and/or
   the inner surface of the joining member comprises a stepped portion disposed between its proximal and distal ends.

14. An ablation probe according to claim 1, wherein the joining member is formed from a tubular member, wherein preferably the joining member comprises a hypotube.

15. An ablation probe according to claim 1, wherein the body of the joining member comprises one or more weakened portions arranged to increase the flexibility of the joining member.

16. An ablation probe according to claim 1, wherein any one or more of: a) the joining member further comprises a heat transfer structure, the heat transfer structure comprising one or more protrusions extending from the outer surface of the joining member; b) the connector comprises a sealing member, the sealing member arranged to at least partially surround a connection region between the connector and either of the distal portion and proximal portions of the feeding cable; or c) the joining member is formed from a flexible metal alloy, preferably Nitinol.

17. An ablation probe according to claim 1, further comprising:
   a first coolant flow path via which coolant is able to flow; and
   a deformable member arranged to move between an insertion configuration in which insertion of the probe is facilitated and a deployed configuration, wherein a second coolant path, via which coolant is able to flow, is provided by the deformable member when in the deployed configuration.

18. An ablation probe according to claim 17, wherein the ablation probe comprises:
   a. a needle portion comprising the deformable member, the applicator, the distal portion of the feeding cable, at least part of a tube housing at least part of the distal portion of the feeding cable and a distal portion of the first coolant path, and:
b. a catheter portion comprising the proximal portion of the feeding cable, the proximal portion of the first coolant path, and a coolant conduit,
wherein the deformable member is fluidly connected to the coolant conduit at a boundary between the needle portion and the catheter portion and the coolant conduit is preferably a non-deformable coolant conduit.

* * * * *